United States Patent
Zander et al.

(10) Patent No.: US 7,084,286 B2
(45) Date of Patent: Aug. 1, 2006

(54) METHOD FOR PRODUCING CONJUGATED FATTY ACID ESTERS

(75) Inventors: Lars Zander, Duesseldorf (DE); Albert Strube, Neuss (DE); Andreas Heidbreder, Solingen (DE); Alfred Westfechtel, Hilden (DE); Wolfgang Giede, Langenfeld (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 52 days.

(21) Appl. No.: 10/489,017

(22) PCT Filed: Aug. 28, 2002

(86) PCT No.: PCT/EP02/09584

§ 371 (c)(1),
(2), (4) Date: Mar. 8, 2004

(87) PCT Pub. No.: WO03/022964

PCT Pub. Date: Mar. 20, 2003

(65) Prior Publication Data

US 2004/0242909 A1    Dec. 2, 2004

(30) Foreign Application Priority Data

Sep. 6, 2001    (DE)    ................ 101 43 534

(51) Int. Cl.
*C07C 51/347*    (2006.01)
(52) U.S. Cl. .................................... 554/126
(58) Field of Classification Search ................ 554/126
See application file for complete search history.

(56) References Cited

U.S. PATENT DOCUMENTS 6,177,580 B1    1/2001    Timmermann et al.

FOREIGN PATENT DOCUMENTS

| DE | 197 18 245 C1 | 7/1998 |
| EP | 0 950 410 A1 | 10/1999 |
| GB | 1 408 189 A | 10/1975 |
| WO | WO 00/09163 A1 | 2/2000 |

OTHER PUBLICATIONS

Nichols P L Jr et al: "Isomers of conjugated fatty acids. I. Alkali-isomerized linoleic acid" Journal of the American Chemical Society, American Chemical Society, Washington, DC, US, vol. 73, No. 1, Jan. 24, 1951, pp. 247-252, XP002130752 ISSN: 0002-7863.
Nutrition, vol. 19, Nr. 6 (1995)—not enclosed—reciting entire book.
Chin et al., "Dietary Sources of Conjugated Dienoic Isomers of Linoleic Acid, a Newly Recognized Class of Anticarcinogens", Journal of Food Composition and Analysis, 5, Academic Press, Inc., (1992), pp. 185-197.
Dieckelmann et al., The Basics of Industrial Oleochemistry, ISBN 3-89355-008-9, (1988), pp. 52-81.

*Primary Examiner*—Deborah D. Carr
(74) *Attorney, Agent, or Firm*—John F. Daniels

(57) ABSTRACT

Processes for preparing conjugated fatty acid products are described wherein (a) a composition which comprises a fatty acid ester having at least two unconjugated, carbon-carbon double bonds is provided; (b) the fatty acid ester is conjugated in the presence of a water-free base; (c) phosphoric acid is added to the conjugated fatty acid ester such that phosphate salts are precipitated; and (d) the precipitated phosphate salts are removed.

20 Claims, No Drawings

METHOD FOR PRODUCING CONJUGATED FATTY ACID ESTERS

BACKGROUND OF THE INVENTION

Unsaturated fatty acids are important constituents of natural fats. One of their most important representatives is linoleic acid which is a C18 acid with two double bonds. In 1978, researchers at the University of Wisconsin discovered that isomers of this fatty acid where the double bonds are conjugated have particularly beneficial effects on health. These isomeric octadecadienoic acids are collectively referred to in the scientific literature as conjugated linoleic acids (abbreviation: CLA) and have recently attracted increasing attention (NUTRITION, VOL.: 19/NR. 6 1995). They are responsible for a reduction in the fatty content of tissue and support the build up of muscle. In addition, they are said to be anti-carcinogenic and to stimulate the immune system.

Conjugated linoleic acids are present as constituents in various foods. Their principal sources are animal foods, although significant quantities of CLA are also present in milk and dairy products. In addition, CLA have also been found in various oils and fats, their concentration in vegetable oils being significantly lower than in animal fats (J. Food Compos. Anal. 5, 185–197 (1992)).

Since the content in these foods can vary considerably, efforts have been made to add synthetically produced conjugated linoleic acid to foods. EP 0 950 410 A1 discloses a process for isomerizing linoleic acid in the form of an alkyl ester rich in linoleic acid with a strong base, preferably with alkali metal alcoholates, in a water-free medium. The alkyl esters are obtained as described in the book by G. Dieckelmann and H. J. Heinz "The Basics of Industrial Oleochemistry" (ISBN 3-89355-008-9).

The conjugated linoleic acid or the corresponding ester is worked up by neutralization with an acid in aqueous solution. It has been found that, where esters are subjected to the isomerization, a higher yield of conjugated linoleic acid is obtained. Accordingly, the isomerization is generally carried out on the methyl ester using alkali metal methanolates. After the addition of water and acid, phase separation occurs, the conjugated linoleic acid being obtained as the organic phase.

Where working up is carried out in this way, however, the problem generally arises after isomerization that the soaps formed during the reaction prevent clearly defined phase separation when water is added because an emulsion is formed. In addition, the aqueous phase is contaminated by the methanol released which has to be removed at considerable expense for environmental reasons.

Now, the problem addressed by the present invention was to provide a process which would simplify the isolation of conjugated alkyl fatty acid esters after isomerization. Thus, the reaction solution would be prevented from foaming intensively or forming emulsions. In addition, the use of solvents would be limited or avoided altogether; in particular, no water-solvent mixtures would be formed. The purity of the end products would also be increased, i.e. products with a relatively low acid value would be obtained.

BRIEF SUMMARY OF THE INVENTION

The present invention relates, in general, to a process for the production of conjugated fatty acid esters with improved working up of the reaction mixture.

The present invention relates to a process for the production of conjugated unsaturated fatty acid esters, in which a) strong water-free bases are added to unconjugated unsaturated fatty acid esters containing 12 to 22 carbon atoms and at least 2 double bonds in the fatty acid component and 1 to 5 carbon atoms in the alcohol component, so that unconjugated unsaturated fatty acid esters are isomerized, b) phosphoric acid is added to the conjugated fatty acid esters obtained and c) the phosphate salts precipitated are removed from the reaction mixture.

In this way, no ester cleavage occurs after the isomerization step. In addition, the absence of water and soaps in this process means that there is no formation of any two-phase system which would be difficult to work up because of emulsification, i.e. no phase separation.

DETAILED DESCRIPTION OF THE INVENTION

Fatty acid esters containing 16 18 carbon atoms and at least 2 double bonds in the fatty acid component and 1 to 5 carbon atoms in the alcohol component are preferably used. In a particularly preferred embodiment, the fatty acid esters used are linoleic acid esters containing 1 to 5 carbon atoms in the alcohol component Of these fatty acid esters, linoleic acid methyl ester and linoleic acid ethyl ester are particularly preferred. Oils containing linoleic acid selected from the group consisting of sunflower oil, thistle oil, soybean oil, cottonseed oil, peanut oil, rapeseed oil and palm oil may also be used as starting product for the production of conjugated fatty acid esters in accordance with the invention after conversion of the free fatty acids into the esters with alcohols containing 1 to 5 carbon atoms.

In a preferred embodiment, alkali metal alcoholates containing 1 to 10 carbon atoms are used as bases during the isomerization phase. Where phosphoric acid is added, alkali metal phosphates precipitate from the reaction solution and can readily be removed. The alcohol formed during the reaction of phosphoric acid with alkali metal alcoholates may readily be distilled off in vacuo. Accordingly, no contaminated solvents so expensive to dispose of are formed in the production process.

Particularly preferred bases are potassium methanolate, potassium ethanolate or potassium-t-butylate. The potassium phosphate formed after the addition of phosphoric acid where these two bases are used has the most favorable precipitation properties and leads to almost complete removal of the potassium ions from the reaction mixture. The alcohols methanol, ethanol or t-butanol formed after addition of phosphoric acid can be distilled off quickly without intensive foaming.

85% phosphoric acid is preferably used for precipitation of the phosphate salts because, in this way, very little water is introduced into the reaction mixture and the phosphoric acid can still be handled by virtue of its high viscosity. To promote the precipitation reaction, the reaction mixture is heated to 40 to 130° C., preferably to 80 to 120° C. and more particularly to 100 to 120° C.

In another preferred process, water-free bases are added to fatty acid esters containing 12 to 22 carbon atoms and at least two unconjugated double bonds in the fatty acid component and 1 to 5 carbon atoms in the alcohol component in order to isomerize the fatty acid esters, after which glycerol is added dropwise to the reaction solution. Phosphoric acid is added to the conjugated fatty acid triglycerides obtained and the phosphate salts precipitated are removed from the reaction mixture.

EXAMPLES

Example 1

Preparation of Conjugated Sunflower Oil Methyl Ester 1,200 g sunflower oil methyl ester were dried before conjugation. 24 g potassium methanolate were then added. The temperature was increased to 130° C. and the mixture was stirred for 2.5 to 3 hours at that temperature. The mixture was then cooled to 110° C. and carefully neutralized with 85% phosphoric acid, the solution changing color from red-brown to yellow. The temperature was increased to 120° C. and the mixture stirred in vacuo for 30 mins. at 120° C. Slight foaming was observed to begin with, but soon disappeared. The product was cooled to 40° C. and freed from the potassium salts by filtration on Hyflow. 1% Ethoxyquin was added for stabilization. The conjugated sunflower methyl ester thus obtained had an acid value of 8 (as determined to ISO 660).

Example 2

Preparation of Conjugated Sunflower Oil Methyl Ester with Working Up Using Water 10 g 30% sodium methanolate were added to 443 g sunflower oil methyl ester. The mixture was stirred for 5 hours at 111 to 115° C. in a closed reactor. The reaction solution was cooled to 100° C. and 100 ml water, to which 4 g citric acid had been added, were added.

The reaction solution foamed intensively to begin with and then formed an emulsion which did not allow complete phase separation. In this way, only lightly conjugated sunflower oil methyl ester with an acid value of 15 (as determined to ISO 660) could be isolated.

Example 3

Preparation of Conjugated Sunflower Triglycerides 265 g sunflower oil methyl ester were dried before conjugation. 5.3 g potassium methanolate were then added. The temperature was increased to 130° C. and the mixture was stirred for 3 hours at that temperature. 10 g glycerol were added dropwise to the solution and the methanol released was distilled off in vacuo. The mixture was then cooled to 110° C. and carefully neutralized with 85% phosphoric acid, the solution changing color from red-brown to yellow. The temperature was increased to 120° C. and the mixture was stirred in vacuo for 30 minutes at 120° C. Slight foaming was observed to begin with, but soon disappeared. The product was cooled to 40° C. and freed from the potassium salts by filtration on Hyflow. 1% Ethoxyquin was added for stabilization.

What is claimed is:

1. A process for preparing conjugated fatty acid products, said process comprising:
    (a) providing a composition which comprises a fatty acid ester having at least two unconjugated, carbon-carbon double bonds;
    (b) conjugating the fatty acid ester in the presence of a water-free base;
    (c) adding phosphoric acid to the conjugated fatty acid ester such that phosphate salts are precipitated; and
    (d) removing the precipitated phosphate salts.
2. The process according to claim 1, wherein the fatty acid ester comprises a fatty acid portion having from 12 to 22 carbon atoms and a fatty alcohol portion having from 1 to 5 carbon atoms.
3. The process according to claim 1, wherein the fatty acid ester comprises a fatty acid portion having from 16 to 18 carbon atoms and a fatty alcohol portion having from 1 to 5 carbon atoms.
4. The process according to claim 1, wherein the fatty acid ester comprises a linoleic acid alkyl ester.
5. The process according to claim 4, wherein the linoleic acid alkyl ester is selected from the group consisting of linoleic acid methyl ester, linoleic acid ethyl ester and mixtures thereof.
6. The process according to claim 1, wherein the fatty acid ester comprises linoleic acid methyl ester.
7. The process according to claim 1, wherein the water-free base comprises an alkali metal alcoholate.
8. The process according to claim 2, wherein the water-free base comprises an alkali metal alcoholate.
9. The process according to claim 4, wherein the water-free base comprises an alkali metal alcoholate.
10. The process according to claim 1, wherein the water-free base comprises an alkali metal alcoholate having from 1 to 10 carbon atoms.
11. The process according to claim 7, wherein the alkali metal alcoholate comprises a component selected from the group consisting of methanolates, ethanolates, t-butanolates, and mixtures thereof.
12. The process according to claim 7, wherein the alkali metal alcoholate comprises a potassium alcoholate.
13. The process according to claim 7, wherein the alkali metal alcoholate comprises a component selected from the group consisting of potassium methanolate, potassium ethanolate, potassium t-butanolate, and mixtures thereof.
14. The process according to claim 1, wherein the phosphoric acid is added as an aqueous solution having a concentration of 85% or more.
15. The process according to claim 1, further comprising adding glycerol to the conjugated fatty acid ester whereby a conjugated fatty acid glyceride is obtained via transesterification and the phosphoric acid is added to the conjugated fatty acid glyceride.
16. The process according to claim 15, further comprising removing alcohol produced during the transesterification.
17. The process according to claim 1, wherein the composition comprises a sunflower oil alkyl ester.
18. The process according to claim 1, wherein the composition comprises a sunflower oil methyl ester.
19. A process for preparing conjugated fatty acid products, said process comprising:
    (a) providing a composition which comprises a linoleic acid alkyl ester having at least two unconjugated, carbon-carbon double bonds;
    (b) conjugating the fatty acid ester in the presence of an alkali metal alcoholate;
    (c) adding an aqueous solution of phosphoric acid having a concentration of 85% or more to the conjugated fatty acid ester such that phosphate salts are precipitated; and
    (d) removing the precipitated phosphate salts.
20. A process for preparing conjugated fatty acid products, said process comprising:

(a) providing a composition which comprises a linoleic acid alkyl ester having at least two unconjugated, carbon-carbon double bonds;
(b) conjugating the fatty acid ester in the presence of an alkali metal alcoholate;
(c) adding glycerol to the conjugated fatty acid ester whereby a conjugated fatty acid glyceride is obtained via transesterification and removing alcohol produced during the transesterification;
(d) adding phosphoric acid to the conjugated fatty acid glyceride such that phosphate salts are precipitated; and
(e) removing the precipitated phosphate salts.

* * * * *